US009431227B2

United States Patent
Jong

(10) Patent No.: US 9,431,227 B2
(45) Date of Patent: *Aug. 30, 2016

(54) SAMPLE TRANSFERRING APPARATUS FOR MASS CYTOMETRY

(71) Applicant: FLUIDIGM CANADA INC., Markham (CA)

(72) Inventor: Raymond Jong, Toronto (CA)

(73) Assignee: Fluidigm Canada Inc., Markham (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/594,319

(22) Filed: Jan. 12, 2015

(65) Prior Publication Data

US 2015/0122991 A1    May 7, 2015

Related U.S. Application Data

(63) Continuation of application No. 13/661,686, filed on Oct. 26, 2012, now Pat. No. 8,963,076.

(60) Provisional application No. 61/551,470, filed on Oct. 26, 2011.

(51) Int. Cl.
    *H01J 49/10*    (2006.01)
    *H01J 49/04*    (2006.01)
    *G01N 35/10*    (2006.01)
    (Continued)

(52) U.S. Cl.
    CPC .......... *H01J 49/0445* (2013.01); *G01N 35/10* (2013.01); *H01J 49/045* (2013.01); *H01J 49/105* (2013.01); *G01N 15/06* (2013.01); *G01N 2015/0065* (2013.01)

(58) Field of Classification Search
    USPC .......... 250/281, 282, 286, 287, 288
    See application file for complete search history.

(56) References Cited

U.S. PATENT DOCUMENTS 5,170,052 A    12/1992    Kato
5,969,352 A    10/1999    French et al.
(Continued)

FOREIGN PATENT DOCUMENTS

WO    02/054075 A1    7/2002
WO    2005/003767 A2    1/2005
WO    2005/093874 A1    10/2005

OTHER PUBLICATIONS

Baranov et al., "A Sensitive and Quantitative Element-Tagged Immunoassay with ICPMS Detection", Analytical Chemistry, Apr. 1, 2002, vol. 74, No. 7, pp. 1629-1636.
Baranov et al., "The Potential for Elemental Analysis in Biotechnology", Journal of Analytical Atomic Spectrometry, 2002, 17, pp. 1148-1152.
(Continued)

*Primary Examiner* — Nicole Ippolito
*Assistant Examiner* — Hanway Chang
(74) *Attorney, Agent, or Firm* — Kilpatrick Townsend & Stockton LLP

(57) ABSTRACT

In a mass cytometer or mass spectrometer, a sample of elemental tagged particles is transferred from a dispersion to a gas flow through a carrier aerosol spray for atomization and ionization by inductively coupled plasma (ICP) source. The configuration of the sample transfer apparatus allow for total consumption of the sample by passing the sample spray through a deceleration stage to decelerate the spray of particles from its high velocity expansion. Following the deceleration stage, the decelerated sample of particles can be accelerated and focused through an acceleration stage for transferring into the ICP. This effectively improves the particle transfer between the sample spray and the ICP.

10 Claims, 7 Drawing Sheets

(51) Int. Cl.
  *G01N 15/00* (2006.01)
  *G01N 15/06* (2006.01)

(56) References Cited

U.S. PATENT DOCUMENTS

| | | |
|---|---|---|
| 6,242,735 B1 | 6/2001 | Li et al. |
| 7,135,296 B2 | 11/2006 | Baranov et al. |
| 7,479,630 B2 | 1/2009 | Bandura et al. |
| 7,700,295 B2 | 4/2010 | Baranov et al. |
| 7,767,407 B2 | 8/2010 | Baranov et al. |
| 8,481,925 B2 | 7/2013 | Antonov et al. |
| 8,963,076 B2 * | 2/2015 | Jong .................... 250/282 |
| 2004/0011953 A1 | 1/2004 | Chen et al. |
| 2004/0072250 A1 | 4/2004 | Baranov et al. |
| 2005/0218319 A1 | 10/2005 | Bandura et al. |
| 2009/0050801 A1 | 2/2009 | Fedorov |
| 2011/0024615 A1 | 2/2011 | Tanner |

OTHER PUBLICATIONS

Liu et al., "Method for Quantitative Proteomics Research by Using Metal Element Chelated Tags Coupled with Mass Spectrometry", Analylical Chemistry, Sep. 15, 2006, vol. 78, No. 18, pp. 6614-6621.

Lou et al., "Polymer-Based Elemental Tags for Sensitive Bioassays", Angew. Chern. Int. Ed., 2007, 46, pp. 6111-6114.

Vancaeyzeele et al., "Lanthanide-Containing Polymer Nanoparticles for Biological Tagging Applications: Nonspecific Endocytosis and Cell Adhesion", Journal of the American Chemical Society, 2007, 129, pp. 13653-13660.

International Search Report regarding corresponding PCT/IB2012/002568, dated Feb. 15, 2013, 4 pages.

Written Opinion of the International Searching Authority, PCT/IB2012/002568, dated Feb. 15, 2013, 4 pages.

European Search Report mailed on Aug. 27, 2015 for EP Patent Application No. 12844611.9, 7 pages.

* cited by examiner

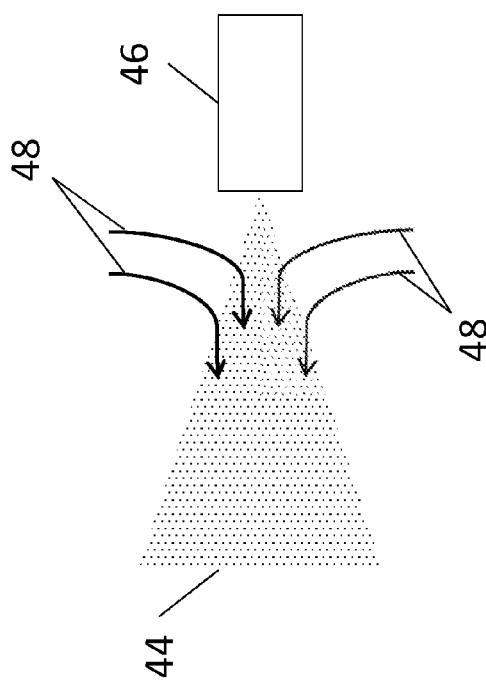
FIG. 2A – Prior Art
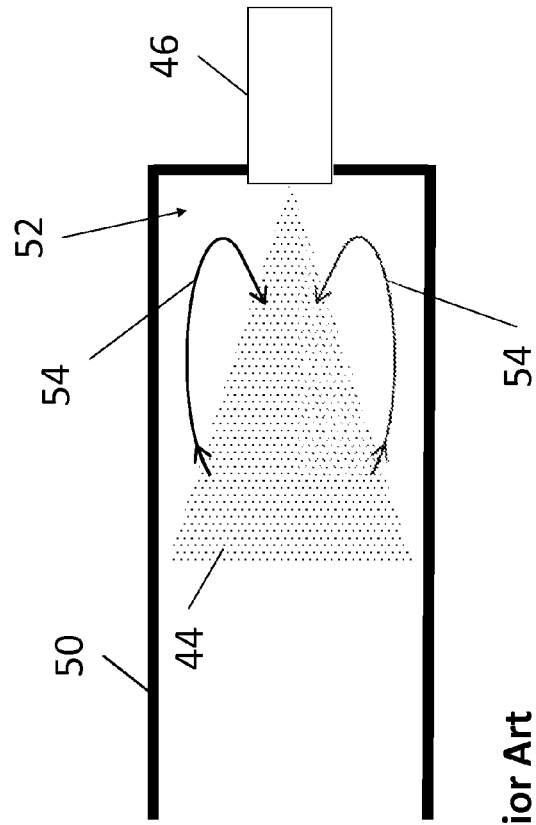
FIG. 2B – Prior Art

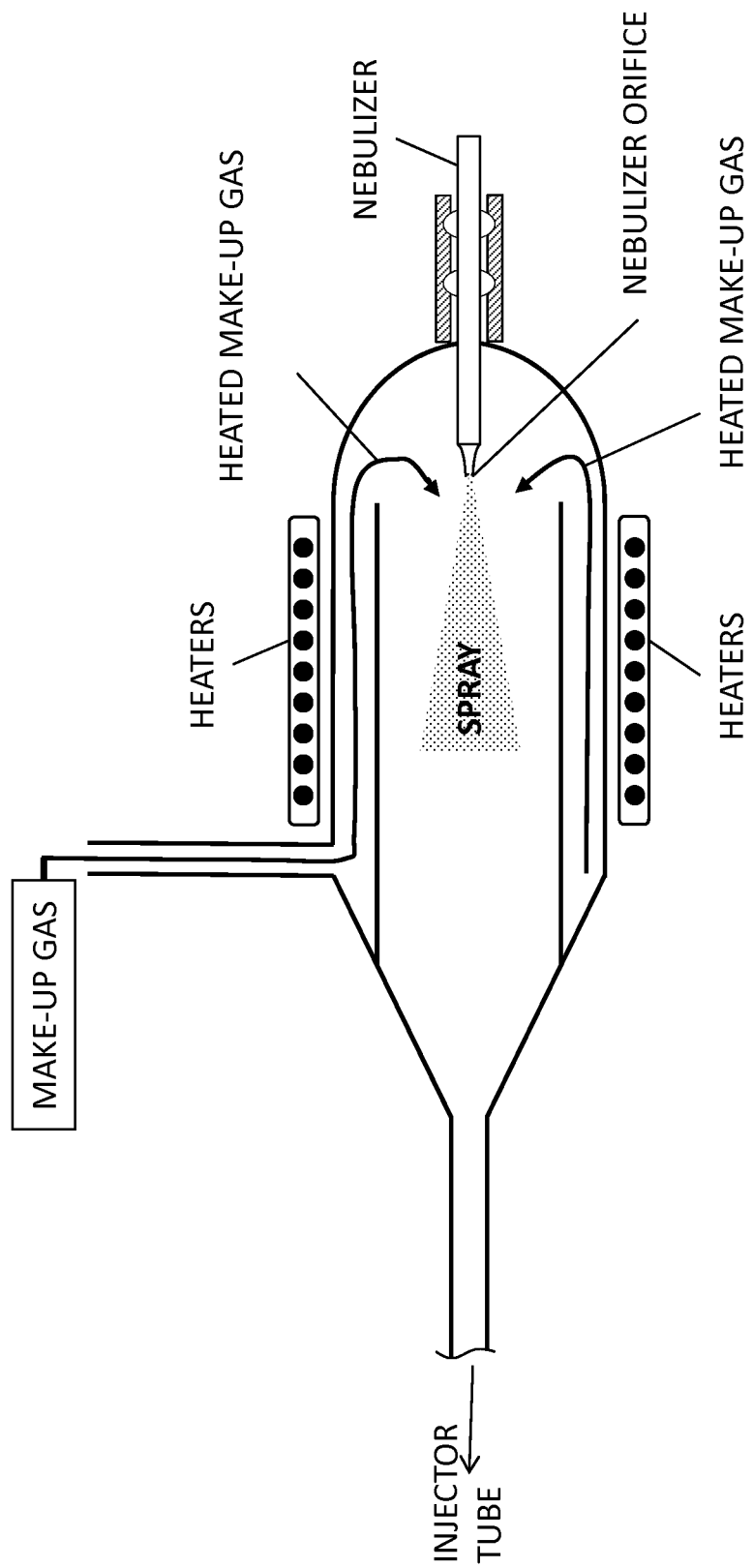
FIG. 3 – Prior Art

SAMPLE TRANSFERRING APPARATUS FOR MASS CYTOMETRY

This application in a Continuation of U.S. application Ser. No. 13/661,686, filed on Oct. 26, 2012, which claims benefit under 35 U.S.C. §119(e) of U.S. Provisional Application No. 61/551,470, filed on Oct. 26, 2011.

FIELD

This invention relates to apparatus and methods for transferring particles in a sample for mass cytometry.

INTRODUCTION

One application for mass cytometry is directed to single particle analysis where cells or other particles of interest are labeled with metal-conjugated antibodies and metallointercalators and introduced individually into an Inductively Coupled Plasma (ICP) ion source, where the cells are atomized and ionized. The atomic ions are extracted, separated by mass and quantitatively measured in the mass cytometer (MC). The mass cytometer can be, for instance, a mass spectrometer adapted to quantitatively measure the number of each of various different ions per cell. The quantitative measurements for multiple different types of ions can be conducted concurrently, as described in U.S. Pat. No. 7,479,630. The elemental signature of the cell is represented by the element tags associated with the antibodies and metallointercalators. The presence of the metal tag indicates that the antibody conjugated with that tag found and bound the target biomarker, and the intensity of the signal corresponding to that ionized tag is directly proportional to the number of corresponding antibodies bound per cell.

The samples dissolved in solution that are typically introduced into an ICP are delivered pneumatically by forming an expanding spray, of relative high velocity, which subsequently undergoes droplet size sorting, anti-coalescence measures and/or condensation removal before being ionized. Although these techniques can work efficiently for the typical samples, they have several short comings when transferring a dispersion containing particles of elemental tagged cells or beads suspended in an aqueous solution for individual particle analysis by mass cytometry.

SUMMARY

In view of the foregoing, the present teachings provide an apparatus for transferring a dispersion of particles in a sample spray for mass analysis. The apparatus comprises a decelerator tube having an inlet end adapted to receive the sample spray generated from a nebulizer, for example, a pneumatically assisted nebulizer, and a confinement passage downstream of the inlet end to decelerate the spray. The inlet end of the decelerator tube can be closed around the sample spray to enclose the spray along the decelerator tube's confinement passage from external gas. In conjunction with the closed inlet end, the sample spray recirculates into itself along the confinement passage thereby resulting in a decelerated sample spray emerging from a discharge end located downstream of the confinement passage. The apparatus also comprises an elongate accelerator chamber having an entrance end concentrically space out from the discharge end and the discharge end is positioned within the entrance end. An outlet end is displaced downstream of the entrance end to define a flow acceleration channel between the two ends. The elongate accelerator chamber has a gas inlet port adapted to receive a sheath gas, supplied by sheath gas source. The gas inlet port has a flow path with the entrance end for passing the sheath gas into the flow acceleration channel. The acceleration channel and the outlet end can have a configuration to form a pressure reduction through the outlet end, so as to accelerate the sheath gas, and along with it the emerging decelerated sample spray, through the outlet end. In various embodiments, the acceleration channel can be a conical bore channel with a constriction through the outlet end.

Additionally, the present teachings provide a system for inductively coupled plasma mass cytometry. The system comprises a nebulizer, for example, a pneumatic assisted nebulizer, for generating a sample spray of dispersion of particles. The sample spray of dispersion of particles can be directed to a sample transfer device for transferring the sample spray of dispersion of particles. The sample transfer device comprises a decelerator tube for receiving and decelerating the sample spray of dispersion of particles and an elongate acceleration chamber surrounding at least a portion of the decelerator tube for receiving the decelerated sample spray of dispersion of particles. A gas inlet port can pass a sheath gas into the elongate acceleration chamber for accelerating the decelerated sample spray of dispersion of particles. The system further comprises an inductively coupled plasma for ionizing the accelerated sample spray of dispersion of particles and a mass cytometer, for example, a time-of-flight mass analyzer, configured for measuring each isotope corresponding to the particles ionized by the inductively coupled plasma.

The present teachings also provide a method for transferring a sample spray containing elemental tagged particles for analysis by inductively coupled plasma mass cytometry (ICP-MC). The method comprises directing the sample spray into a decelerator tube and confining the sample spray along a predetermined length of the decelerator tube for promoting the sample spray to recirculate. In conjunction with the recirculation, the sample spray is decelerating along the decelerator tube, for example, during a deceleration stage, and the decelerated sample spray is discharged into a flow accelerator chamber. As the decelerated sample spray is discharged, in an acceleration stage a sheath gas is passed around the decelerated sample spray and the sheath gas along with the decelerated sample spray accelerates through a flow acceleration chamber, for example, by providing the flow acceleration chamber with a conical shaped bore tapered towards the acceleration chamber's outlet end. The method further comprises forming a pressure drop through the outlet end to deliver the accelerated sample and sheath gas to the ICP-MC.

Another aspect of the invention is an apparatus for transferring a dispersion of particles in a sample spray for mass analysis. The apparatus has a decelerator tube having an inlet end adapted to receive the sample spray and a confinement passage downstream of the inlet end. The inlet end is closed around the sample spray to promote spray recirculation and spray deceleration in the confinement passage. The decelerator tube has a discharge end transition downstream from the confinement passage to pass the decelerated sample spray. The apparatus also has an elongate accelerator chamber having an entrance end concentrically spaced out from the discharge end of the decelerator tube. The discharge end of the decelerator tube is positioned within the entrance end of the accelerator chamber. An outlet of the accelerator chamber is displaced downstream of the entrance end to define a flow acceleration channel therebetween.

Yet another aspect of the invention is an apparatus for transferring a sample spray containing elemental tagged particles into an inductively coupled plasma mass cytometer (ICP-MC). The apparatus has a decelerator tube having an inlet end adapted to receive the sample spray and a confinement passage downstream of the inlet end. The inlet end is closed around the sample spray. The decelerator tube has a discharge end transition downstream from the confinement passage. The apparatus also has an elongate accelerator chamber having an entrance end concentrically spaced out from the discharge end of the decelerator tube. The discharge end of the decelerator tube is positioned within the entrance end of the accelerator chamber. The accelerator chamber has an outlet end displaced downstream of its entrance end to define a flow acceleration channel therebetween. The flow acceleration channel has a conical shaped bore tapered towards the outlet end. The elongate accelerator chamber has a gas inlet port adapted to receive a sheath gas. The gas inlet port has a flow path with the entrance end.

Another aspect of the invention is a system for inductively coupled plasma mass cytometry. The system has a nebulizer for generating a sample spray of a dispersion of particles and a sample transfer device for transferring the sample spray of dispersion of particles. The sample transfer device has a decelerator tube for receiving and decelerating the sample spray of dispersion of particles. An elongate acceleration chamber surrounds at least a portion of the decelerator tube for receiving the decelerated sample spray of dispersion of particles. The system has a gas inlet port for passing a sheath gas into the elongate acceleration chamber for accelerating the decelerated sample spray of dispersion of particles and an inductively coupled plasma for ionizing the accelerated sample spray of dispersion of particles. A mass cytometer is configured for measuring each isotope corresponding to the particles ionized by the inductively coupled plasma.

Another aspect of the invention is a method for transferring a dispersion sample spray containing elemental tagged particles for analysis by inductively coupled plasma mass cytometry (ICP-MC). The method includes directing the dispersion sample spray into a decelerator tube. The dispersion sample spray is confined along a predetermined length of the decelerator tube for decelerating the sample spray. The decelerated dispersion sample spray is discharged from the decelerator tube. A sheath gas is passed around the discharged decelerated dispersion sample spray. The sheath gas and the discharged decelerated dispersion sample are accelerated through a flow acceleration chamber and into the ICP-MC.

Still another aspect of the invention is a sample transfer device for transferring a dispersion of particles in a sample spray into an instrument for mass analysis by a mass spectrometer. The apparatus has a decelerator for receiving the sample spray from a nebulizer. The decelerator is adapted to promote spray recirculation and spray deceleration in a confinement passage defined by the decelerator and to conduct the spray from the nebulizer through the confinement passage to a decelerator outlet at the opposite end of the confinement passage. An accelerator is positioned to receive the spray from the decelerator outlet. The accelerator is adapted to accelerate the spray away from the decelerator through an accelerator outlet. One application of the sample transfer device is for use in a system including an inductively coupled plasma adapted to receive the accelerated sample spray of dispersion of particles from the accelerator outlet and produce elemental ions from the particles and a mass cytometer adapted to measure at least some of the elemental ions produced from the particles by the inductively coupled plasma.

These and other features of the present teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way. In the accompanying drawings:

FIG. 2A is a schematic diagram showing the distribution of a typical sample spray from a prior art nebulizer and showing surrounding gas entrained therein;

FIG. 2B is a schematic diagram similar to that of FIG. 2A but showing the aerosol as being confined in a tube and with recirculation;

FIG. 3 is a schematic diagram of a prior art spray chamber;

In the drawings, like reference numerals indicate like parts.

DESCRIPTION OF VARIOUS EMBODIMENTS

It should be understood that the phrase "a", "an", "the" or "said" used in conjunction with the present teachings with reference to various elements encompasses "one or more" or "at least one" unless the context clearly indicates otherwise. The terms "comprising", "including" and "having" and variations thereof are intended to be inclusive and mean that there may be additional elements other than the listed elements. Moreover, the use of "forward" and "rearward", "up" and "down", and variations of these terms, or the use of other directional and orientation terms, is made for convenience, but does not require any particular orientation of the components.

Figure 1:
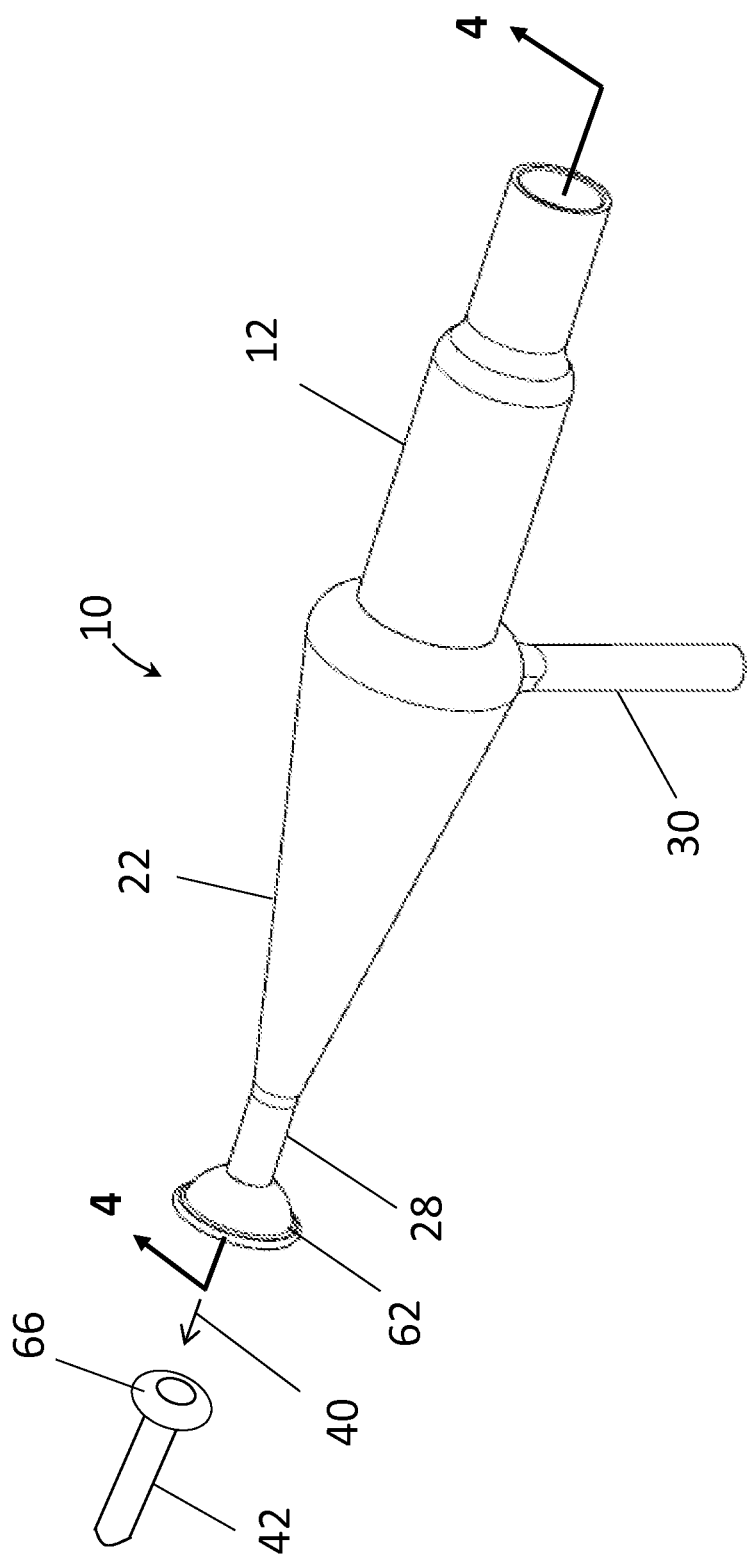
FIG. 1 is a perspective view of one embodiment of a sample transferring device of the present teachings.
Figure 4:
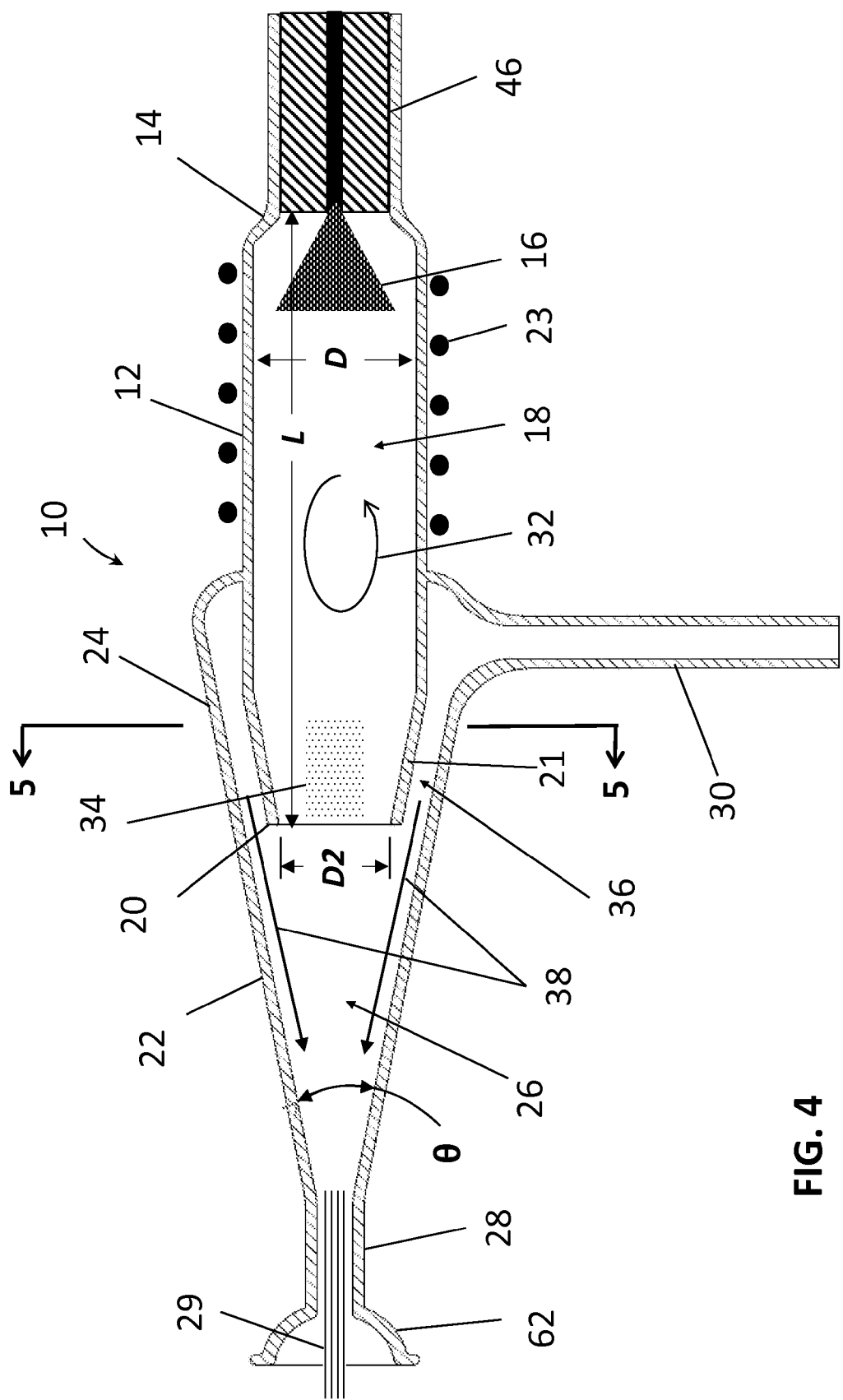
FIG. 4 is a cross sectional view of the device illustrated in FIG. 1 taking in a plane including line 4-4 on FIG. 1 showing the transferring of the sample spray through the various stages of the sample transferring device.

Reference is first made to FIGS. 1 and 4, which show one embodiment of a sample transferring device, generally indicated by reference number 10. The sample transferring device 10 includes a decelerator tube 12 for reducing the velocity of a sample spray 16 in a deceleration stage and an elongate accelerator chamber 22 positioned downstream of the decelerator tube 12, for accelerating the spray in an acceleration stage. A gas inlet port 30 connected to the elongate accelerator chamber 22 at its upstream end provides a conduit for passing a sheath gas 38 (FIG. 4) into the end of the accelerator chamber 22 adjacent the decelerator tube 12 to accelerate the decelerated sample spray as will be described below. As illustrated in FIG. 4, the downstream end of the decelerator tube 12 extends into the accelerator chamber 22 so the outlet 20 of the decelerator tube is downstream from the upstream end of the accelerator chamber. The gas inlet port 30 is suitably upstream from the outlet 20 of the decelerator tube, as illustrated in FIG. 4. The terms elongate accelerator chamber and accelerator chamber are used interchangeably for the present teachings. Although the accelerator chamber in the illustrated embodiment is elongate, it is understood that the accelerator chamber is not required to be elongate within the broad scope of the invention. The accelerator chamber 22 further comprises an outlet end 28 arranged downstream of the decelerator tube 12 so that the accelerated sample spray travels in the direction indicated by the arrow 40 on FIG. 1 and converges into a small diameter injection tube 42 which conducts the sample to the Inductively Coupled Plasma.

To help understand how an expanding sample spray can be decelerated from its high velocity expansion, in a deceleration stage, and then converged towards an injector tube, reference is now made to FIG. 2A and FIG. 2B, each of which illustrates a prior art device. A sample spray 44, also referred to an aerosol spray, can be conveniently produced by a conventional pneumatic nebulizer 46, and can be characterized by an expanding jet of gas, vapor, droplets and particles associated with the sample. As described in U.S. Pat. No. 5,969,352 (the '352 patent), which shares a common inventor with the present application, an expanding aerosol spray 44 in an unconfined space (such as is illustrated in FIG. 2A) tends to have the property of entraining the surrounding free gas adjacent the base of the jet so the jet includes the entrained gas, as indicated by arrows 48. Because the spray 44 is unconfined, no recirculation of any part of the spray occurs and all of the spray's entrainment needs are supplied by the surrounding gas. When the sample spray 44 is formed in a confined space however, such as in the sealed end of a tube 50 having a closed end 52 that is substantially sealed to the opposite end of the tube 50 from any external supply of gas, as shown in FIG. 2B, there is insufficient free gas available for entrainment and therefore part of the aerosol spray 44 downstream from the base of the jet is drawn upstream back into the jet near its base to supply the gas needed by the expanding jet through recirculation as indicated by arrows 54 on FIG. 2B. The recirculation has, as described by the '352 patent, an undesirable effect on the droplets in the periphery of the aerosol spray 44. These periphery droplets rejoin the main aerosol spray 44 at a much slower velocity than that of the main sample spray 44, and as such, collide with the faster moving droplets, leading to coalescence of droplets into undesirably large sizes and undesirable and memory effects.

Accordingly, the solution offered by the '352 patent is to provide make-up gas to supply enough gas to the otherwise closed end of the tube to prevent or reduce the recirculation before collecting the spray into a small diameter injector tube. As shown in FIG. 3, which represents a spray chamber of the '352 patent, the nebulizer and its spray is located in the path of the make-up gas. Further, contrary to the device previously shown in FIG. 2B, the end of the spray chamber in FIG. 3 is not sealed from external supply of gas and instead relies on introduction of make-up gas from external of the spray chamber to avoid recirculation. The make-up gas, having been preheated by the heaters, is directed at the expanding spray and at the nebulizer orifice allowing the spray to entrain the heated make-up gas directly. The resulting heat transfer aids in evaporating the liquid droplets while the spray propagates downstream towards the injector tube.

The present inventors have observed in the above prior art configuration illustrated in FIG. 3 that the spray tends to retain its initial high velocity distribution as the spray undergoes a transition towards the injector tube. While successful up to a point, some of the high velocity droplets are undesirably lost due to impact with the spray chamber's inner surface or vapor is undesirably condensed onto the surface of the spray chamber as the spray cools. Furthermore, although the entrainment of the heated make-up gas reduces droplet coalescence and aids evaporation, the thermal heat transfer between the make-up gas and the spray can cause analytical signal abnormalities when using certain types of samples. In some circumstances, excessive heat can disrupt the particle's integrity resulting in cell fragmentation, for example, giving rise to signal peak spreading.

Rather than follow the teachings in the '352 patent, the applicants have recognized that by promoting a dispersion of particles in a sample spray to recirculate, the individual particles can be decelerated during a deceleration stage to a velocity distribution level suitable for subsequent acceleration in an acceleration stage followed by delivery of the accelerated spray into the ICP. With reference to the sample transferring device 10 illustrated in FIG. 4, the inlet end 14 of the decelerator tube 12 can be configured such that the nebulizer 46, or an ancillary part of the nebulizer, closes the inlet end 14 of the decelerator tube 12 around the sample spray 16 so the decelerator tube has a closed end to enclose the sample spray along the length of the decelerator tube 12 to its opposite outlet end 20 from any external source of gas. While the inlet end 14 can be adapted in this closed end configuration for receiving the sample spray 16, the spray directed into the decelerator tube can expand along a confinement passage 18 and recirculate into itself. For visual clarity, the recirculation pattern is indicated by the arrow 32 in FIG. 4 while the sample spray 16 is pictorially shown localized upstream of the arrow 32. Although the recirculation 32 and sample spray 16 are illustrated separately in FIG. 4, it is understood that the recirculation is not separate from the spray. Generally, the propagation of the confined sample spray 16 and the recirculation 32 can coexist along the length of the confinement passage 18.

The particles associated with the sample spray 16, in accordance with the present teachings, can be any discrete object of a size suitable for mass analysis by a mass spectrometer. In various embodiments, for example, particles can include viral microorganisms (viruses), biological cells or beads, any of which can be tagged with one or more metal element, such as Au, Eu, Ir and the lanthanides to name a few. For brevity, the terms particles and elemental tagged particles are used interchangeably herein. As discussed above, a pneumatic nebulizer is a suitable device for transferring the dispersion of suspended particles into a spray. Within a dispersion sample, the particles are generally suspended in an aqueous solution, and when the sample is nebulized into the form of a spray, the dispersion's individual and discrete particle separation is maintained. This is contrary to a sample in solution where the sample is dissolved typically in a solvent (e.g. acetonitrile, methanol) or in an acidic solution and the generated spray contains the dissolved sample within droplets or as vapor. According to the present teachings, the dispersion's sample spray, for example, can be an aerosol spraying at a rate of about 60,000 particles per minute, with a mean particle diameter of about 10 µm, and in an aqueous carrier solution spray rate of about 60 μL/min. In many circumstances, when using a sample transfer device 10 as described herein, this sample flow rate can be totally consumed by the ICP. Generally, the droplet size distribution in the spray 16 as a function of the radial distance from the central axis of the spray suggests that the droplet size increases toward the periphery of the spray pattern. Thus, the particles generally tend to be found predominately at the periphery of the spray 16. As the sample spray 16 expands into the decelerator tube 12, the particles from the periphery of the spray tend to recirculate back into the spray 16 at a slower velocity. The recirculation can be repeated over a distance along the confinement passage 18 resulting in discharging a decelerated sample spray of decelerated particles generally indicted at 34 from the decelerator outlet 20.

In the example described above, the decelerator tube 12 can be defined by its recirculation distance which can further be defined by a predetermined length L of the confinement passage 18, as shown in FIG. 4. The length L of the confinement passage 18 is suitably in the range of about 22 mm to about 70 mm. The confinement passage 18 can also be conveniently defined by a bore characterized by its diameter D. As illustrated in FIG. 4, the diameter D is the maximum diameter of the decelerator tube 12. The diameter D of the decelerator 12 is suitably in the range of about 15 mm to about 22 mm. In accordance with the applicant's teachings, each of the dimensions for the length L and for the bore diameter D can, independently or in combination such as its relative ratio (length:diameter), contribute to the extent of sample spray deceleration. The dimensions for the length L and the bore diameter D can be selected in accordance with the profile of the sample spray 16.

For example, for a typical pneumatic nebulizer operating with a nebulizer gas flow rate of about 0.2 L/min at about 344 kPa (50 psi) back pressure, the circumferential edge of an unconfined spray can have a diameter of about 2 cm measured at a location 3 cm, for example, downstream from the point of spray formation. Generally, the spray angle of such unconfined spray is likely to remain constant while the spray diameter continues to increase as the spray propagates further downstream. When the spray 16 within the decelerator tube 12 is produced by this same nebulizer, however, the spray angle can be affected due to the velocity reduction of the recirculating particles. Moreover, the circumferential edge of the confined spray can become less defined as the sample spray 16 evolves downstream for passage through the discharge end 20 of the decelerator tube 12. Accordingly, a lower limit for the relative ratio of length:diameter can be expressed by the unconfined spray profile at a length L of 3 cm to a bore diameter D of 2 cm, or equivalently a ratio of length:diameter of 1.5. Constructing a decelerator tube 12 can be based on the relative ratio of length:diameter of 1.5 and applied to initial predetermined values for either diameter D or length L. For example, in various embodiments, while the confinement passage 18 can be selected to have a predetermined diameter D between 15 mm and 22 mm, the predetermined length L can be chosen to provide between about 22 mm and 33 mm of recirculation distance to produce corresponding length to diameter ratio of about 1.5.

The applicants recognize that the relative ratio between the length and diameter, length:diameter, used to select the dimensions of the decelerator tube 12 can be increased to a value that is higher than 1.5 so that there can be a longer deceleration stage distance for the sample spray 16 to further reduce its velocity profile before the particles are focused in the acceleration stage downstream in the elongate accelerator chamber 22. For example, the sample spray 16 as described above can be decelerated and discharged for focusing using a decelerator 12 having a predetermined bore diameter D and length L of about 17 mm and 70 mm respectively. In this exemplary embodiment, the length: diameter ratio is about 4. The range of the relative ratio length:diameter is suitably between about 1.5 and about 4. While the forgoing is an exemplary range of the ratio of length:diameter, the properties of the unconfined aerosol spray can, as determined by the nebulizer gas flow rate and back pressure, define the lower limit for selecting a predetermined diameter D. In various embodiments, for example, a range of ratio of length:diameter between 3 to 4 can be required for an aerosol spray generated with a nebulizer back pressure greater than 344 kPa (50 psi). Generally, additional embodiments with length:diameter greater than 4 are contemplated with consideration given to other factors as will be discussed later.

According to FIG. 4, the discharge end 20 of the decelerator 12 is shown to have a taper transition 21 having a narrow end diameter at the outlet that is less than the bore diameter D. For example, the diameter D2 at the decelerator outlet in suitably about 14 mm while the bore diameter D is about 20 mm. The shape of the taper transition 21 can be selected to accommodate the internal geometry of the flow acceleration channel 26 of the accelerator chamber 22. For example, the taper transition can suitably have a shape selected so the annular space 36 between the acceleration chamber 22 and the taper transition 21 at the outlet end of the decelerator 12 has a uniform thickness, as illustrated in FIG. 4.

Figure 5:
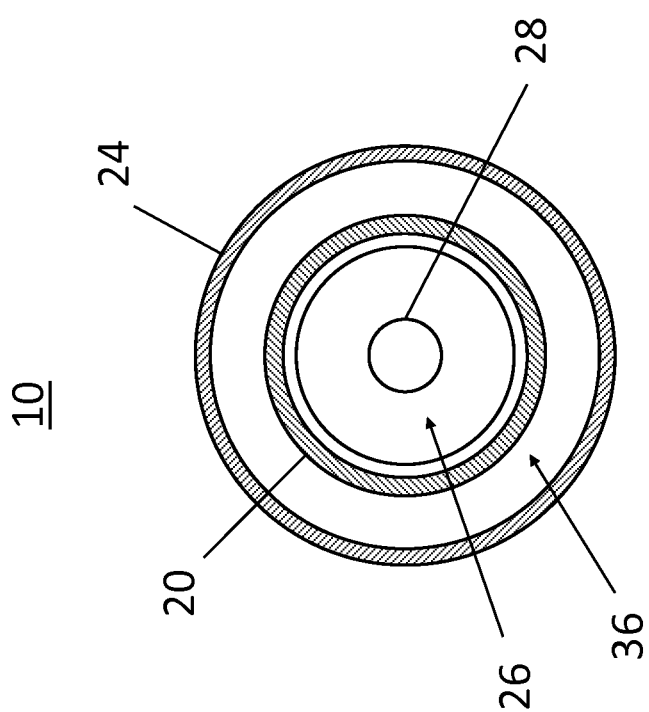
FIG. 5 is a cross sectional view of the device illustrated in FIGS. 1 and 4 taken in a plane including line 5-5 on FIG. 4.
Figure 6:
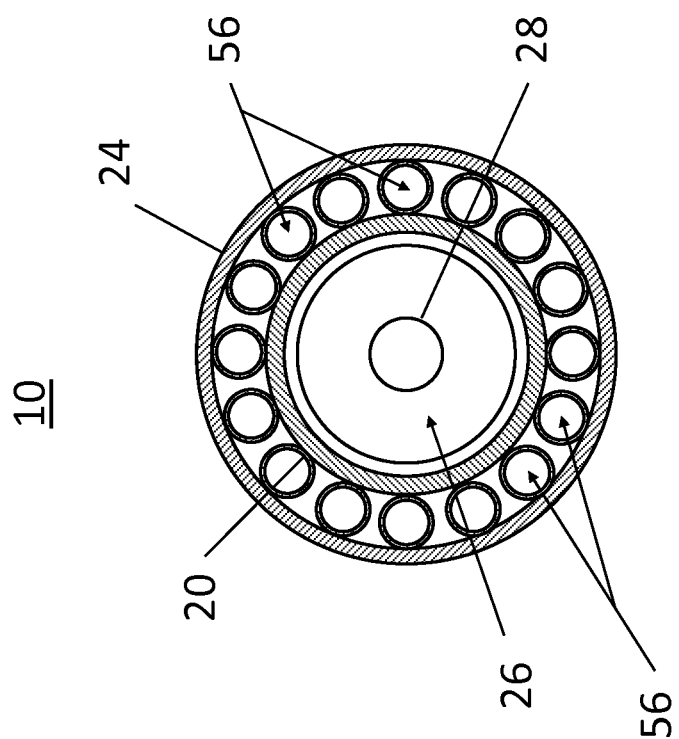
FIG. 6 is a cross sectional view similar to that of FIG. 5 but showing an embodiment that includes multiple sheath gas flow channels circumferentially spaced around the discharge end.
Figure 8:
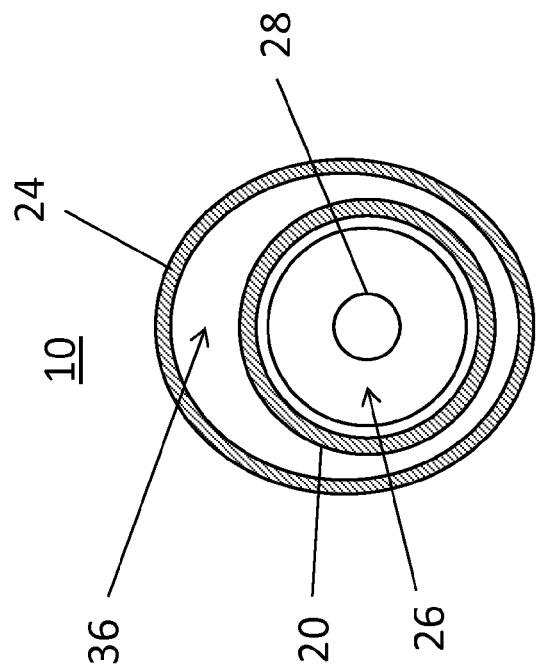
FIGS. 7 & 8 are cross sectional views similar to that of FIG. 5 showing various embodiments that have different cross sectional shapes at the entrance end according to the present Teaching.
Figure 7:
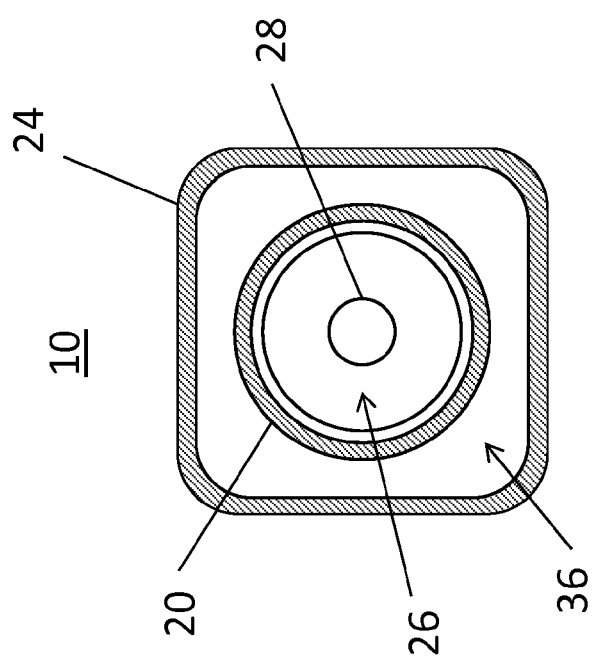

The accelerator chamber 22 can have an entrance end 24 that surrounds at least a portion of the decelerator tube's 12 discharge end 20 in such a way that the discharge end 20 is positioned within the entrance end 24. As illustrated in FIG. 4, for example, the outlet end of the decelerator 12 extends into the accelerator chamber 22 at its entrance end 24. In various embodiments, for example, the entrance end 24 can be in concentric alignment with the discharge end 20 of the decelerator 12, so that the entrance end 24 can be radially spaced out from the discharge end 20. The concentric space or gap between the two ends defines an annular channel 36 as shown in FIGS. 4 and 5. An external sheath gas source, not shown, can supply a sheath gas (e.g., argon, nitrogen, or other gas that has limited or no effect on the measurement) to a gas inlet port 30 connected to the entrance end 24 of the accelerator chamber 22. As illustrated in FIG. 4, the flow path between the inlet port 30 and the annular channel 36 allows the sheath gas 38 to flow from the inlet port 30, into the entrance end 24, through the annular space 36, and then along the flow acceleration channel 26 of the accelerator 22.

The configuration of flow acceleration channel 26 can have a conical shaped bore with an elongate taper towards the outlet end 28. Generally, during the acceleration stage, as the flow of sheath gas 38 propagates downstream in the accelerator from the entrance end 24 along the flow acceleration channel 26 and towards the outlet end 28, the gas velocity increases as the cross sectional area of the conical-bore shaped channel 26 decreases. The configuration of the outlet end 28 can be defined as a constriction relative to the overall conical bore of the flow acceleration channel 26. Thus, the conical bore as shown in FIG. 4 tends to accelerate the flow of sheath gas 38 to a higher velocity as it passes through the constriction geometry of the outlet end 28. Not unlike the venturi effect, a pressure reduction through the constriction can have the effect of accelerating the movement of gas through the flow acceleration channel 26.

Accordingly, at the interface where the decelerated sample spray 34 emerges from the exit end 20 of the decelerator tube 12, the spray 34 is captured by the sheath gas 38 within the accelerator chamber 22. The sheath gas 38 surrounds the emerging decelerated sample spray 34 and accelerates the sample of particles contained within towards the outlet end 28. The accelerated combination of sheath gas and sample particles passing through the outlet end 28 of the accelerator for transferring to the ICP is generally indicated at 29. The applicants recognized that when the flow acceleration channel's conical profile is elongate, as shown in FIG. 4, the gas flow streamlines associated with the sheath gas 38 tends to be laminar and contracts radially inward with minimum turbulence. Particles that can enter the streamlines with a velocity distribution profile sufficiently low to minimize crossing the path of the laminar flow streamlines can be collimated by the sheath gas 38 flow. In various embodiments, for example, the elongate acceleration chamber can be defined by the cone angle θ (FIG. 4) of the conical bore, as a measured of the taper. A cone angle θ of about 20 degrees can provide the acceleration chamber with sufficient elongation to sustain conditions for smooth gas flow streamlines with minimum or low turbulence. Any turbulent mixing at the interface between the sheath gas 38 and the emerging spray 34 can be dampened as the mixing propagates downstream. Consequently, the accelerating sheath gas 38 can maintain particle focusing and convergence downstream through the outlet end 28 for transferring into the ICP injection tube 42. The focusing and acceleration of the particles and other spray material in the accelerator 22 also helps draw the particles and other spray materials into a thin line, which can be advantageous because it can reduce the likelihood that two particles will arrive at the ICP at the same time.

As illustrated in FIGS. 1 and 4, the device 10 suitably has a formation 62 at the outlet end 28 adapted to help align the ICP injection tube 42 with the outlet. For example, the formation 62 in the illustrated embodiment is generally a rounded funnel shape. The ICP injection tube suitably has a corresponding formation 66 that generally conforms to the funnel-shaped formation 62 on the device. Although the formations 62, 66 in the illustrated embodiment are rounded (e.g., ball and socket type formations) other formations that can be used to help alignment are contemplated as being within the scope of the invention.

While the present teachings are described in conjunction with various embodiments, it is not intended that the present teachings be limited to such embodiments. On the contrary, the present teachings encompass various alternatives, modifications, and equivalents, as will be appreciated by those of skill in the art. For example, the present applicants recognize that the ratio length:diameter can be chosen to be greater than 4, particularly for applications in which there is greater tolerance for potential wetting effects on the internal surface of the confinement passage 18. In various embodiments, the decelerator tube 12 can be heated by a heater/heating element 23 (FIG. 4) to elevate the temperature of the internal surface of the confinement passage 18 for mitigating wetting, for example to about 200 degrees C. Additionally, the elevated temperature of the confinement passage's 18 internal surface can transfer heat to the recirculating particles as the spray 16 decelerates. Accordingly, the heating element 23 can be provided for heating the decelerator tube 12 so that the temperature of the internal surface of the confinement passage 18 can be elevated.

Although the discharge end 20 of the decelerator tube 12 can be configured with a taper transition 21 for the purpose of maintaining a corresponding geometry with the conical bore of the flow acceleration channel 26, the applicants have contemplated the use of a discharge end 20 that is untapered. The taper geometry provides a convenient means of matching the conical profile of the entrance end 24 of the accelerator 22 to establish an equally spaced annular channel 36 for forming a generally uniform sheath gas 38 flowing concentrically around the emerging decelerated spray 34. An alternative geometry for the elongate accelerator chamber 22 can have a portion of the entrance end 24 configured with a non-conical straight section (cylindrically linear) to accommodate a complementary straight or cylindrically linear discharge end 20. A sheath gas 38 flowing through a non-tapering annular channel's 36 may transition into the accelerator channel's conical bore with no or little turbulence.

Furthermore, in various embodiments, the flow of sheath gas 38 can be delivered through more than one inlet port or distributed from one or more than one inlet port 30 through multiple channels 56 extending through the annular space 36 as shown in FIG. 6. Each of the channels 56 can be arranged around the circumference of the discharge end 20 to deliver a combined sheath gas flow downstream of the channels 56. In this exemplary embodiment, the discharge end 20 of the decelerator tube 12 can be positioned within the entrance end 24 of the accelerator so that the exit face of the discharge end 20 and the exit faces of the channels 56 can generally be in alignment or out of alignment. The channels can help maintain laminar flow through the annular space 36 between the decelerator 12 and the accelerator 22 and can help minimize turbulence in the accelerator.

Additionally, in various embodiments, the cross section of the entrance end 24 of the accelerator 22 can be a quadrilateral, such as the square profile shown in FIG. 7, or the cross section can be oval as shown in FIG. 8. As shown in FIG. 8, the oval entrance end 24 of the accelerator 22 can generally be non-concentrically positioned relative to the discharge end 20 of the accelerator such that the annular channel 36 can be asymmetrical. Non-concentric positioning can also be used with entrance ends that are square or circular in cross section if desired. When an asymmetrical annular channel 36 is used, the flow of sheath gas 38 through the various portions of the channel can be non-uniform. If desired, the shape of the conical acceleration chamber 22 can be modified in a corresponding manner. Generally, the function of the pneumatically assisted nebulizer 46 is for transferring the elemental tagged cells or other particles as defined above from a carrier solution into an aerosol suspension for ICP injection. Other types of nebulizers have been considered by the applicants and can be accommodated in the present teachings. In various embodiments, for example, an ultrasonic nebulizer that utilizes a vibrating surface to atomize a sample solution can be adapted for use in the present teachings. This type of nebulizer produces a fine aerosol plume without the use of a gas jet. A plume of particles with low momentum can be directed into the decelerator tube 12 for transport downstream into the elongate accelerator chamber 22. A carrier gas can be used to aid in directing the plume into the closed inlet end 14. Alternatively, an ultrasonic driven surface can be positioned within the decelerator tube 12 to directly generate a plume of particles within. Since the inlet end 14 remains closed around the plume and with the absence of a nebulizing gas flow in the decelerator tube 12, the plume can be drawn from the decelerator tube 12 into the accelerator chamber by the reduced pressure created by the accelerating sheath gas 38 flow. Furthermore, a drop-on-demand type of nebulizer, similar to the type used for inkjet printing technology, is contemplated by the applicants of the present teachings. Other desired types of aerosol-generating devices known to the skilled person in the art may be used, and the aerosol-generating device can create an aerosol at atmospheric pressure, above atmospheric pressure, near atmospheric pressure, or less than atmospheric pressure.

In various embodiments, the sample transferring device 10 can be fabricated from a chemically inert material such as glass or quartz, for example. Generally, the elongate accelerator chamber can be manufactured by drawing down a glass chamber into a conical-shaped bore having a length of about 80 to about 100 cm and having a diameter for the constricting outlet end 28 of about 4 to about 6 mm. Although the cone angle θ has been described as about 20 degrees, the applicants have contemplated cone angles θ greater than 20 degrees and less than 20 limited only by the criteria that the gas flow streamlines retain their laminar or near laminar conditions.

Figure 9:
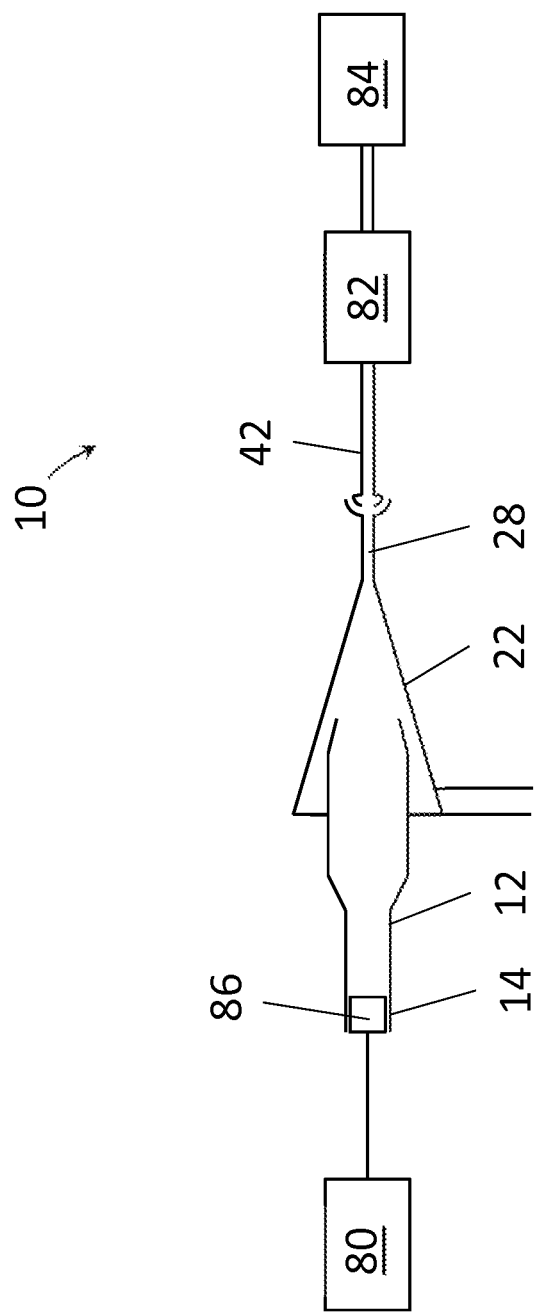
FIG. 9 is a schematic diagram of the device illustrated in FIGS. 1 and 4 in combination with an ICP-MS instrument.

The present invention is described in conjunction with transferring particles, such as elemental tagged cells or beads into an ICP for mass cytometry. Referring to FIG. 9, the transferring device 10 is illustrated in a schematic diagram connected to a sample supply 80 (e.g., a syringe pump) for supplying a sample containing dispersed particles to the nebulizer 46 mounted in the closed end 14 of the decelerator 12 of the device 10. The outlet 28 of the accelerator 22 is connected to a conduit 42 that leads the accelerated particles from the device 10 to the ICP 82. The ICP 82 is suitably connected to a mass spectrometer 84 in a conventional manner. The mass cytometer 84 can be based on, for example, a Time-Of-Flight (TOF) or a magnetic sector (Sector) mass analyzer configured for simultaneously measuring each isotope corresponding to the multi-target individual particles ionized by the ICP. Alternatively, the mass analyzer can be a scanning quadrupole (Q) or linear ion trap (LIT) based mass spectrometer system where the particles can be measured sequentially. Generally, scanning analyzers require a settling time between individual isotope measurements and the time period tends to be longer than the duration of the transient ion cloud produced in the ICP from an individual particle. Thus, measurements of two or more isotopes during a transient event of individual particle analysis are therefore not likely practical with these scanning types of mass analyzers. However, in various embodiments, the quadrupole and ion trap based mass spectrometers can be limited to bulk analysis of elemental tagged cells in accordance with the present teachings. Accordingly, the sample transferring device can be used for ICP mass cytometry based on TOF, Sector, Q, LIT, or a combination thereof.

In various embodiments, the particle being transferred from the sample dispersion by the gas flow of the aerosol and being directed through the sample transfer device 10 can pass through an intermediate stage prior to injection into the ICP. The intermediate stage can include, for example, a means of concentrating or increasing the cross sectional particle density along the direction of travel 40. Alternatively, a means of increasing particle separation after the sample transfer device 10 can be employed to reduce particle overlapping in the ICP. The density of the particles per unit length can be increased by increasing the cross sectional flow area for the stream of particles and sheath gas as it enters the ICP 84. Conversely, particle separation can be increased by decreasing the cross sectional area for the flow of particles and sheath gas.

Aspects of the applicant's teachings may be further understood in light of the following example, which should not be construed as limiting the scope of the present teachings in any way.

EXAMPLE

Table 1 shows the bead count from a commercial ICP mass cytometer system, manufactured by DVS Sciences Inc., for particles introduced with the sample transfer device 10 according with the present teachings and with a prior art spray chamber. A sample dispersion of Europium 151 (Eu151) tagged beads in a concentration of 4.35E+05 beads per milliliter dispersed in water was atomized with a nebulizer flow rate of 0.20 L/min argon gas and supplemented with a sheath gas or a make-up gas flow rate of 0.86 L/min argon gas.

TABLE 1

| Sample Transfer Device | Mean Eu151 counts | CV: Eu151 |
|---|---|---|
| BSC device | 1972 | 22 |
| NSC device | 2153 | 15 |

The particle count is generally represented by a discrete of a normal population distribution as a result from detecting the presence of the elemental tag, Eu151. The coefficient of variation (CV) of the mean count is an indication of how well the particles are distinctly detected by the mass cytometer. Generally, a lower CV value can indicate fewer particles being undetected or that fewer particles can be detected incompletely resulting in signal peak spreading. The CV for the transfer device 10 of the present teaching (the NSC device) is about 15% while the CV for the prior art spray chamber (the BSC device) is about 22%. The lower CV value demonstrates the ability to achieve better transfer of the particles in the sample dispersion for ICP mass cytometry in accordance with the present teachings.

As various changes could be made in the above without departing from the scope of the invention, it is intended that all matter contained in the above description and shown in the accompanying drawings shall be interpreted as illustrative and not in a limiting sense.

The invention claimed is:

1. A method for transferring a dispersion sample spray containing elemental tagged particles for analysis by inductively coupled plasma mass cytometry (ICP-MC), wherein the method comprises:
    directing a dispersion sample spray into a decelerator tube;
    confining the dispersion sample spray along a length of the decelerator tube and decelerating the dispersion sample spray;
    discharging the decelerated dispersion sample spray from the decelerator tube;
    passing a sheath gas around the discharging decelerated dispersion sample spray;
    ionizing the dispersion sample spray; and
    directing the ionized dispersion sample spray into a mass spectrometer for analysis.

2. The method of claim 1, comprising recirculating the dispersion sample spray within the decelerator tube.

3. The method of claim 2, comprising heating the recirculated dispersion sample spray.

4. The method of claim 1, comprising heating the decelerator tube.

5. A system for mass cytometry comprising:

a mass spectrometer; and a sample transfer device for transferring a dispersion of particles in a sample spray into the mass spectrometer, wherein the sample transfer device comprises:
- a decelerator comprising a decelerator inlet, a decelerator outlet and a confinement passage extending from the inlet to the outlet, wherein, the inlet is configured to receive a sample spray from a nebulizer; and
- the decelerator is configured to receive the sample spray; and
- the decelerator is configured to decelerate the sample spray;
- an ionizer positioned to receive the decelerated sample spray from the decelerator outlet and is configured to ionize the sample spray to provide elemental ions for analysis by a mass spectrometer.

6. The system of claim 5, wherein the decelerator is sealed between the nebulizer and the decelerator outlet.

7. The system of claim 5, wherein the confinement passage is characterized by a length and a diameter, wherein a ratio of the diameter to the length is from 1.5 to 5.

8. The system of claim 5, wherein the mass spectrometer comprises a time-of-flight mass analyzer.

9. The system of claim 5, wherein the mass spectrometer comprises a quadrupole mass analyzer.

10. The system of claim 5, wherein the mass spectrometer comprises a magnetic sector mass analyzer.

\* \* \* \* \*